(12) United States Patent
Gong et al.

(10) Patent No.: US 7,312,197 B2
(45) Date of Patent: Dec. 25, 2007

(54) METHOD OF MODIFYING GLUCOSE ACTIVITY USING POLYPEPTIDES SELECTIVELY EXPRESSED IN FAT TISSUE

(75) Inventors: Da-Wei Gong, Olney, MD (US); John McLenithan, Baltimore, MD (US); Alan Shuldiner, Columbia, MD (US); Rongze Yang, Baltimore, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 523 days.

(21) Appl. No.: 10/785,720

(22) Filed: Feb. 24, 2004

(65) Prior Publication Data

US 2004/0220099 A1 Nov. 4, 2004

Related U.S. Application Data

(60) Provisional application No. 60/449,489, filed on Feb. 24, 2003.

(51) Int. Cl.
C07K 14/435 (2006.01)
A61K 38/17 (2006.01)

(52) U.S. Cl. ............................. 514/12; 514/2; 530/350; 530/399

(58) Field of Classification Search .................... None
See application file for complete search history.

(56) References Cited

U.S. PATENT DOCUMENTS

| | | | |
|---|---|---|---|
| 6,146,849 | A | 11/2000 | Pierce et al. |
| 6,342,581 | B1 | 1/2002 | Rosen et al. |
| 6,478,825 | B1 | 11/2002 | Winterbottom et al. |
| 6,635,255 | B1 | 10/2003 | Bruck et al. |
| 2002/0173635 | A1 | 11/2002 | Jacobs et al. |
| 2003/0064412 | A1 | 4/2003 | Fischer et al. |
| 2004/0044191 | A1 | 3/2004 | Fischer et al. |

FOREIGN PATENT DOCUMENTS

| | | |
|---|---|---|
| WO | 99/49033 | 9/1999 |
| WO | 99/60161 | 11/1999 |
| WO | 00/05367 | 2/2000 |
| WO | 00/66708 | 11/2000 |
| WO | 00/73454 A1 | 12/2000 |
| WO | 01/16318 | 3/2001 |
| WO | 01/68848 A2 | 9/2001 |
| WO | 02/068579 A2 | 9/2002 |

OTHER PUBLICATIONS

Yang et al.: cDNA Cloning, Genomic Structure, Chromosomal Mapping, and Functional Expression of a Novel Human Alanine Aminotransferase. *Genomics*, Mar. 2002; 79(3): pp. 445-450.
Kashiwagi et al.: In Vitro Insulin Resistence of Human Adipocytes Isolated From Subjects With Noninsulin-Dependent Diabetes Mellitus. *J Clin Invest*, Oct. 1983; 72(4): pp. 1246-1254.
Tsuji et al.: Human Intelectin Is a Novel Soluble Lectin That Recognizes Galactofuranose in Carbohydrate Chains of Bacterial Cell Wall. *The Journal of Biological Chemistry*, Jun. 2001, vol. 276, No. 26, pp. 23456-23463.
Lee et al.: Human Homologs of the Xenopus Oocyte Cortical Granule Lectin XL35. *Glycobiology*, 2001, vol. 11, No. 1, pp. 65-73.
Suzuki et al.: Molecular Cloning and Functional Expression of a Human Intestinal Lactoferrin Receptor. *Biochemistry*, 2001, vol. 40, pp. 15771-15779.
Komiya et al.: Cloning of the Novel Gene Intelectin, Which is Expressed in Intestinal Paneth Cells in Mice. *Biochemical and Biophysical Research Communication*, 1998, vol. 251, pp. 759-762.
Altschul et al.: Gapped Blast and PSI-Blast: A New Generation of Protein Database Search Programs. *Nucleic Acids Research*, 1997, Vo. 25, pp. 3389-3402.

*Primary Examiner*—Christine J. Saoud

(57) ABSTRACT

Isolated omentin polypeptides that selectively express in omental fat tissue and methods for the use of the polypeptides. The polypeptides can be used in a method for modifying insulin action and/or glucose metabolism in an animal. The polypeptides can be used to promote glucose uptake by animal adipocytes and other cells, tissues, and/or organs. The polypeptides can also used to provide a therapeutic treatment for diseases of or related to glucose metabolism and adipose tissues. The polypeptides are also incorporated into diagnostic tests and testing kits for diagnosing or detecting a disease or condition involving animal tissue that contains, uses, or expresses the polypeptide in an animal suspected of having the disease or condition.

19 Claims, 9 Drawing Sheets

**100X Omental Fat
Preimmnune antibody**

**100X Omental Fat
Omentin antibody**

**200X Subcutaneous Fat
Omentin antibody**

**200X Omental Fat
Omentin antibody**

METHOD OF MODIFYING GLUCOSE ACTIVITY USING POLYPEPTIDES SELECTIVELY EXPRESSED IN FAT TISSUE

CROSS REFERENCE TO RELATED APPLICATION

This application claims priority from U.S. provisional patent application Ser. No. 60/449,489, filed on 24 Feb. 2003. The priority provisional patent application is hereby incorporated by reference herein in its entirety and is made a part hereof, including but not limited to those portions which specifically appear hereinafter.

GOVERNMENT INTEREST

This invention was made with government support under NIH Grant Number DK57835, awarded by the National Institutes of Health. The U.S. Government may have certain rights in the invention.

FIELD OF INVENTION

The present invention relates to isolated polypeptides that selectively express in fat tissue, as well as methods for use of the polypeptides.

BACKGROUND OF THE INVENTION

Obesity affects a growing number of the U.S. population and often is closely associated with insulin resistance, type 2 diabetes, cardiovascular disease, and dyslipidemia. Obesity itself is typically a heterogeneous condition, due to regional distribution of fat tissue. Central obesity generally refers to fat accumulation in omental or visceral cavity, whereas peripheral obesity generally refers the subcutaneous fat accumulation. Epidemiological studies have established that central obesity is associated with a higher degree of risk than peripheral obesity to the above-mentioned diseases, however, the underlying mechanism(s) are generally not well understood. Presumably, distinctive biological properties of omental fat, in addition to its unique anatomical location, contribute to the increased pathogenecity of central obesity. It has been discovered that an excess of cortisol can cause central obesity and that treatment of HIV patients with protease inhibitor can lead to accumulation of omental fat accumulation but depletion of subcutaneous fat. In vitro studies have also demonstrated that abdominal visceral fat pads can be relatively resistant to the anti-lipolytic effect of insulin and susceptible to the lipolytic effect of catecholamine. At a molecular level, omental fat has been shown to have increased gene expression or secretion of interleukin 6, plasminogen activator inhibitor (PAI-1), and angiotensinogen, compared to subcutaneous fat. These observations indicate the existence of biological difference between omental and subcutaneous fat depots Adipose, i.e., fat, tissue plays a critical role in the pathogenesis of obesity and its associated diseases, but the molecular mechanisms for these associations generally remain unclear. Adipose tissue is generally recognized as an important endocrine organ that communicates actively with the central nervous system and other peripheral tissues through the release of a variety of bioactive factors that regulate glucose and lipid homeostasis. These factors, collectively known as adipocytokines, include leptin, tumor-necrosis factor a (TNFα), plasminogen activator inhibitor-1 (PAI-1), adiponectin/ACRP30/adipoQ, and resistin. Adipo-cytokines have been demonstrated to play a key role in the pathogenesis of obesity and its associated diseases. Nevertheless, current knowledge of known genes generally cannot fully explain the pathophysiology of obesity, and effective treatment for these diseases is still lacking.

Adipose tissue also plays a central role in energy homeostasis. Its primary function is to store and mobilize energy in the form of triglycerides in response to caloric excess and deprivation, respectively. Adipose tissue can be divided into white adipose tissue (WAT) and brown adipose tissue (BAT). WAT and BAT are different in morphology and biological function; WAT is monolocular and mainly functions in storing triglyceride, while BAT is multilocular, rich in mitochondria, and designed to burn energy. BAT is mainly present in hibernating animals, rodents and new-born humans, indicating evolutional adaptation of adipose tissue to environment. Because the significance of the BAT to adult physiology is relatively not clear, references herein to adipose tissue or fat cells generally refer to WAT. Central obesity generally refers to intra-abdominal fat accumulation in visceral or omental adipose tissues, although, strictly speaking, omental fat is a subset of visceral fat.

Obesity is due to the excess accumulation of triglyceride in intra-abdominal (omental) and subcutaneous adipose tissue. Studies of animal models have provided some mechanistic understandings of obesity, likely a communication disorder between the central nervous system and the peripheral tissues, particularly adipose tissue. In mice, certain single gene mutations, such as db/db (leptin receptor mutation) and $A^y$ (the agouti protein is homologous to melanocyte stimulating hormone), can cause obesity, suggesting that a defect involving the central nervous system is the cause for the obesity in these animals. Leptin mutations also can cause obesity in mice (ob/ob), and in humans. However, obesity caused by single gene mutations in humans is rare, and obesity in the general population is thought to be of polygenic origin.

The association of type 2 diabetes with obesity has been observed for a long time. Evidence from epidemiological, clinical and experimental studies has demonstrated that obesity is generally the greatest risk factor for insulin resistance and type 2 diabetes and, moreover, visceral obesity is associated with a higher degree of risk than peripheral obesity. The mechanism for the close association is generally not well understood, but it is generally accepted that an excess of fat leads to increasing insulin resistance and/or impaired glucose disposal, which can predispose someone to type 2 diabetes. The pancreas, liver, muscle, fat tissue, and central nervous system are the principal organs involved in regulating glucose and fat metabolism and are likely to participate in the pathogenesis of obesity and type 2 diabetes. However, recent experimental studies indicate that fat tissue can play a relatively major role in the etiology of type 2 diabetes. For example, surgical excision of visceral fat tissue in the rat has been shown to increase insulin sensitivity suggesting that excess fat is a causative factor for type 2 diabetes. In addition, lipodystrophic patients and fat-depleted mice have developed hyperinsulinemia and type 2 diabetes, and surgical implantation of adipose tissue reverses the diabetic phenotype. Also, adipocyte size may be a determinant of body insulin sensitivity, as it has been proposed that small adipocytes confer insulin sensitivity while large ones result in insulin resistance. These and other studies strongly support the premise that adipose tissue can play a central role in the regulation of insulin sensitivity, and in the pathogenesis of type 2 diabetes.

As discussed above, fat cells generally play an active role in energy storage, fatty acid metabolism and glucose homeostasis. To perform this specialized function, the adipocyte expresses a special subset of genes to communicate with the central nervous system and peripheral tissues, and to respond to various neuronal, metabolic and hormonal signals. The adipocyte secretes a number of bioactive substances, collectively known as adipocytokines, such as, for example, leptin, TNFα, PAI-1, adiponectin, and resistin. These adipocytokines function as endocrine, paracrine, and autocrine factors, and have been implicated in obesity and its associated diseases. Some of these adipocytokines are discussed briefly below.

Leptin is a hormone secreted from fat tissue into the circulation that acts to reduce food intake and increase energy expenditure mainly through binding to leptin receptors in the hypothalamus. Leptin secretion is regulated by the energy supply; starvation decreases its expression and secretion, while overfeeding or increased adiposity induces leptin expression. Leptin is therefore a key molecule linking this adipose tissue to the central nervous system and regulating energy homeostasis.

Tumor necrosis factor-alpha (TNFα) is a cytokine produced not only by inflammatory cells but also by adipocytes. TNFα expression has been shown to be elevated in the fat tissue of obese animals and humans. TNFα appears to induce insulin resistance by interfering directly and/or indirectly with insulin signaling pathways in an autocrine or paracrine fashion. The absence of TNFα results in significantly improved insulin sensitivity in obese mice, the mice lacking TNFα receptors appears protected against diabetes to a certain degree, implying that there might be a yet uncharacterized pathway involved in TNFα-induced insulin resistance.

Plasminogen activator inhibitor-1 (PAI-1) is a key pathogenic factor for thrombotic vascular disease. Plasma PAI-1 levels are closely correlated with visceral fat, and gene expression is highly elevated in visceral fat during the development of obesity. TNFα has been shown to induce adipose PAI-1 expression, providing a possible explanation for the association of obesity with cardiovascular disease.

Adiponectin is a hormone secreted exclusively from adipose tissue and is also referred to as ACRP30, AdipoQ, apM1, or GBP28. Adiponectin has been demonstrated to have promising activities potentially for the treatment of obesity and diabetes. Its expression is reduced in the states of obesity and type 2 diabetes, and its replenishment improves insulin sensitivity and prevents diet-induced obesity in rodents, probably by increasing fat oxidation and decreasing triglyceride content in muscle and liver. This effect can result from increased expression of molecules involved in both fatty-acid combustion and energy dissipation in muscle. The mechanisms for these actions are generally not clear. Adiponectin consists of collagenous repeats and a globular domain homologous to complement C1q, and shares structural similarity to TNFα. Interestingly, PPARγ induces, whereas TNFα suppresses, the expression and secretion of adiponectin, suggesting that adiponectin may be a target molecule relaying insulin sensitivity.

Resistin is a hormone typically isolated from differentiated 3T3-L1 adipocytes by screening for genes regulated by the PPARγ agonist rosiglitazone. During adipocyte differentiation, resistin is increasingly expressed but is suppressed by treatment with rosiglitazone. Moreover, ob/ob mice secrete increased amounts of resistin, and recombinant resistin induces insulin resistance. Resistin has therefore been proposed to be a link between obesity and insulin resistance. However, conflicting results have been reported, in which resistin expression was reduced in several obese animal models and was induced by PPARγ agonists. In addition, unlike the high expression of mouse resistin in adipose tissue, the expression of the human counterpart is very low.

There are additional adipocyte-specific/abundant genes, such as is adipsin and angiotensin, acylation stimulating protein, PGAR, and interleukin-6, whose functions in obesity and type 2 diabetes are generally less understood. Nevertheless, the discovery of a myriad of adipose secreted factors has generally established adipose tissue as an endocrine organ. The dystegulation of adipose tissues autocrine, paracrine and endocrine function is likely to disturb energy homeostasis and lead to obesity, type 2 diabetes, dyslipidemia and hypertension.

Abdominal fat is generally more pathogenic than subcutaneous fat. An obvious explanation for this may simply relate to its anatomical location. Visceral adipose tissue drains via the portal venous system, such that liver is fully exposed to and functionally affected by bioactive substances released from this depot. In addition, differences in physiology, biochemistry and gene expression have been observed between omental and subcutaneous fat tissues. Abdominal obesity is predominant in males whereas subcutaneous fat mass is mostly involved in female obesity, indicating that sex hormones may play a role in these differences. Moreover, an excess of cortisol is known to cause central obesity. Finally, a selective increase in visceral fat is a common feature of aging. It has been suggested that these two adipose tissue depots differ in important ways. Omental adipose fat is more metabolically active with respect to lipolysis and lipogenesis. Compared to subcutaneous fat, abdominal fat pads have greater secretion of interleukin 6, plasminogen activator inhibitor (PAI-1), angiotensinogen, and the rate of apoptosis is greater. In contrast, leptin expression is higher in subcutaneous fat tissue than omental fat tissue. Yet, whether these changes discussed above can explain features of insulin resistance syndrome generally remains unclear. Because the pathophysiological basis of this syndrome is likely to be complex, several genes/gene products and pathways may participate in the disease process.

Insulin signaling is a complex and coordinated process involving protein modification, translocation, and compartmentalization. Insulin action is initiated through binding of insulin to the α subunit of insulin receptor (IR), which activates the beta subunit intrinsic receptor tyrosine kinase, resulting in autophosphorylation of insulin receptor β subunit and tyrosine phosphorylation of intracellular target proteins such as IR substrates (IRS-1-4) and Shc, Cbl, Gab-1. Three major signaling pathways are initiated by these intracellular targets: 1) IRS/PI 3-kinase/Akt; 2) CAP/Cbl; and 3) Shc(or Gab)/Ras/MAP kinase.

In the first major pathway, tyrosine-phosphorylated IRS-1 or IRS-2 binds to src-homology 2 domains of intracellular proteins, including p85, a regulatory subunit of phosphatidylinositol 3-kinase (PI 3-kinase). The interaction of IRS and p85 subunits results in the activation of the p110 catalytic subunit of PI 3-kinase, which raises phosphatidylinositol 3,4-bisphosphate and phosphatidylinositol 3,4,5-trisphosphate (PIP3) levels. These second messengers activate phosphoinositide-dependent kinase-1 (PDK-1) to phosphorylate and hence activate Akt (also called protein kinase B) and atypical PKC isozymes.

In the second major pathway, c-Cbl-associated protein (CAP) recruits c-Cbl to the insulin receptor where it is phosphorylated. This protein complex subsequently localizes to lipid raft domains of the plasma membrane called caveola. The SH2-containing adapter protein CRKII and C3G, a guanine nucleotide exchange factor, are then targeted to phosphorylated c-Cbl at the lipid raft. C3G may activate TC 10, a G-protein of the rho family, which is expressed in adipose and muscle tissue. The IRS/PI 3-kinase/Akt and CAP/Cb1 pathways are generally believed to function in concert to upregulate glucose transport in response to insulin.

The third major pathway involves the activation of the p42/44 MAP kinase (mitogen activated protein kinase) cascade. Insulin receptor phosphorylation of both Shc and Gab-1 adaptor proteins leads to Ras activation of multiple kinases resulting in activation of MAP kinase (Erk1 and 2). This pathway is more involved in the mitogenic function of insulin.

Many other factors interact with and modify the efficiency of insulin signaling in a positive or negative manner, which include protein kinases, e.g., AMP-activated kinase, protein kinase C, and IKKβ, phosphatases, e.g., PTP1B, SHIP2, PTEN, and modulators of IR activity, e.g., PC-1.

There is a need for methods of detecting and treating diseases of or relating to adipose tissue and glucose metabolism, such as obesity and type 2 diabetes.

SUMMARY OF THE INVENTION

An object of this invention is to provide a method for modifying insulin action and/or glucose metabolism in an animal, such as, for example, a human.

Another object of this invention is to provide a method for inducing glucose uptake by animal adipocytes.

An additional object of this invention is to provide a therapeutic treatment for diseases of or related to metabolism and/or adipose tissues.

Yet another object of this invention is to provide a method of diagnosing or detecting a disease or condition involving animal tissue that contains, uses, or expresses omentin polypeptide in an animal suspected of having the disease or condition Yet another object of this invention is to provide a method and/or a diagnostic kit for detecting a polypeptide specific to particular fat tissues, such as omental fat tissue, in bodily fluids of an animal.

One object of the invention can be attained, at least in part, through a method of modifying at least one of insulin action and glucose metabolism in an animal. The method includes modifying the amount of omentin polypeptide in the animal. The amount of active omentin polypeptide can be increased in the animal, such as by administering omentin polypeptide to the animal, or decreased in the animal by interfering with the metabolic function of at least a portion of the omentin polypeptide in the animal. In one embodiment of this invention, the amount of omentin polypeptide in the animal is first determined before any modification.

The invention further comprehends a method of detecting omentin polypeptide in bodily fluids of an animal. The method includes contacting a sample of the bodily fluids with at least one antibody that specifically binds to the omentin polypeptide. The antibody bound to the omentin polypeptide in the sample is then detected.

The invention still further comprehends a method of diagnosing or detecting a disease or condition involving animal tissue that contains, uses, or expresses omentin polypeptide in an animal suspected of having the disease or condition. The method includes first contacting a sample of bodily fluid from the animal with a plurality of antibodies adapted to specifically bind omentin polypeptide. The antibody bound to omentin polypeptide in the sample is detected and an amount of omentin polypeptide in the bodily fluid is measured. The amount of omentin polypeptide is compared to a control to diagnose or detect the disease or condition.

The invention still further comprehends a diagnostic kit for use in diagnosing damage, a condition, or disease in tissue containing or expressing omentin polypeptide. The diagnostic kit includes a measurer of an amount of omentin polypeptide in a sample of bodily fluids and an indicator for determining if a measurement taken by the measurer is in a predetermined range associated with damage, a condition, or disease in the tissue.

The invention still further comprehends a method of inducing glucose uptake by animal cells, tissues, and/or organs, such as, for example, adipocytes or adipose tissue. The method includes administering an omentin polypeptide to at least one of the animal and the adipocytes. The administered omentin polypeptide can enhance insulin-mediated glucose transport in the adipocytes and/or activate, either directly or indirectly, the polypeptide kinase Akt/PKB, also referred to herein as "Akt kinase."

As discussed above, obesity is a heterogeneous condition and can be divided into central (omental or visceral) obesity and peripheral (subcutaneous) obesity, based on the location of fat accumulation. Central obesity is more closely associated with insulin resistance, type 2 diabetes and cardiovascular disease than peripheral obesity, but the underlying mechanisms are generally not known, presumably due to the biological and anatomical difference between the two fat depots. In this invention, fat depot-specific secretory factors have been identified, such as, for example, proteins having the amino acid sequences of SEQ ID NO:1 and SEQ ID NO:3, as well as variants thereof, generally referred to herein as "omentin" or "omentin polypeptides." Omentin polypeptides are expressed in the stromal vascular cells derived from omental, but generally not subcutaneous, adipose tissue. Omentin polypeptides enhance insulin-mediated glucose uptake by adipocytes in vitro and improve glucose disposal in vivo. Furthermore, omentin polypeptides activate Akt kinase, both alone and synergistically with insulin. Omentin polypeptides are also detectable in human blood.

Insulin is a pleiotropic hormone with a broad spectrum of biological functions. In particular, it plays a vital role in regulating glucose, lipid and protein metabolism. The maintenance of glucose homeostasis depends on a precise balance between the release of insulin from the pancreas, glucose production from the liver, and insulin-stimulated glucose transport by muscle and adipose tissue. A number of biological factors can alter insulin sensitivity via different mechanisms. Adipocytokines have been demonstrated to either positively, e.g., leptin and adiponectin, or negatively, e.g., TNFα, modulate insulin sensitivity. Omentin polypeptides can enhance insulin-stimulated glucose in 3T3-L1 adipocytes.

As discussed above, adipocytokines generally play a role in regulating energy metabolism and insulin action. Omentin polypeptides are physiological regulators in this regard as well. Omentin polypeptides are secretory factors from stromal vascular cells in the omental depot and are detectable in human blood. Omentin polypeptides are biologically active in enhancing insulin action in vitro and in vivo. Therefore, the omentin polypeptide is an adipokine that can regulate the adipose biology in a depot-dependent manner.

In identifying and purifying omentin polypeptides, 10,437 expressed sequence tags (EST) from a human omental fat library were sequenced. Bioinformatics analysis revealed that one frequently sequenced EST was a potential secretory factor and Northern analyses revealed that this EST was expressed in omental, but not in subcutaneous, adipose tissue both in humans and Rhesus monkeys. In one embodiment of this invention, the omentin polypeptide is 313 amino acids in length. Omentin polypeptides are secreted proteins when expressed in mammalian cells. In addition, omentin polypeptide can be detected in human blood by Western blotting. Immunofluorescence microscopy demonstrates that omentin polypeptides are generally expressed by stromal vascular cells in omental fat.

In one embodiment of this invention, omentin polypeptides enhance insulin-mediated glucose transport in 3T3-L1 adipocytes. In another embodiment of this invention, omentin polypeptides activate the protein kinase Akt/PKB, both in the presence and absence of insulin. Omentin polypeptides also stimulate insulin-mediated glucose transport and Akt phosphorylation in vitro. This activity is believed to explain, at least in part, why the omental adipose tissue continues to accumulate fat despite systemic insulin resistance in obesity. Without intending to be bound by theory, it is believed that omentin polypeptides sensitize adipocytes to insulin by activating components of the insulin signaling pathway and/or inhibiting negative regulators of the pathway. Furthermore, omentin polypeptide levels can be correlated with Visceral fat, increased glucose disposal, and increased prevalence of type 2 diabetes.

In one embodiment of this invention, the gene encoding the omentin polypeptide provides a positional candidate gene for type 2 diabetes because this gene localizes to a region on chromosome 1q22 that has been linked to type 2 diabetes susceptibility in the Old Order Amish and in at least four other populations independently.

As used herein, the terms "omentin," "omentin protein," or "omentin polypeptide" generally refer to a polypeptide having an amino acid sequence with at least 70% identity, preferably at least 80% identity, more preferably at least 90% identity, and desirably at least 95% identity, to the amino acid sequence of either SEQ ID NO:1 or SEQ ID NO:3.

As used herein, the term "animal" is intended to include humans.

Other objects and advantages will be apparent to those skilled in the art from the following detailed description taken in conjunction with the appended claims.

DESCRIPTION OF THE DRAWINGS

FIG. 1A is a multiple tissue Northern analysis blot from a human. FIG. 1B is a Northern blot of adipose tissues from omental and subcutaneous fat depots of five individual humans.

FIG. 2A is a Northern blot of paired omental (O) adipose tissue and inguinal subcutaneous (S) adipose tissue from five individual Rhesus monkeys. FIG. 2B is a Northern blot that shows regional differences in omentin expression in a single Rhesus monkey.

FIG. 8A is omental tissue treated with pre-immune antibody. FIG. 8B is omental tissue treated with omentin antibody. FIG. 8C is subcutaneous tissue treated with omentin antibody. FIG. 8D is omental tissue treated with omentin antibody shown at a greater magnification (200×) than the sample of FIG. 8B (100×).

DESCRIPTION OF PREFERRED EMBODIMENTS

The present invention relates to polypeptides, referred to herein generally as omentin or omentin polypeptide, selectively expressed in human and other animal omental fat depots, and generally not in subcutaneous fat depots, as well as methods of use of the polypeptides.

In one embodiment of the invention, the omentin polypeptide includes an amino acid sequence of SEQ ID NO:1. The nucleotide sequence for the messenger RNA (mRNA) of SEQ ID NO:1 is SEQ ID NO:2. The present invention also includes variants of the polypeptide of SEQ ID NO:1, i.e., polypeptides that vary by conservative amino acid substitutions, whereby a residue is substituted by another with like characteristics.

In one embodiment of this invention, the variant polypeptides for use in the methods of this invention have at least 70% identity, preferably at least 80% identity, more preferably at least 85% identity, more preferably at least 90% identity, and desirably at least 95% identity, to the amino acid sequence of SEQ ID NO:1, over the entire length of SEQ ID NO:1. One preferred homolog of this invention and usable in the methods of this invention is a polypeptide including the amino acid sequence of SEQ ID NO:3. The polypeptide of SEQ ID NO:3 has about 86% similarity and about 84% identity with the polypeptide of SEQ ID NO:1. The nucleotide sequence for the messenger RNA (mRNA) of SEQ ID NO:3 is SEQ ID NO:4.

Polypeptides for use in the methods of this invention can be prepared in any suitable manner. Such polypeptides include isolated naturally occurring polypeptides, recombinantly produced polypeptides, synthetically produced polypeptides, and/or polypeptides produced by a combination of these methods. As will be appreciated by one skilled in the art following the teachings herein provided, various means for preparing such polypeptides are available in the art.

Figure 1A:
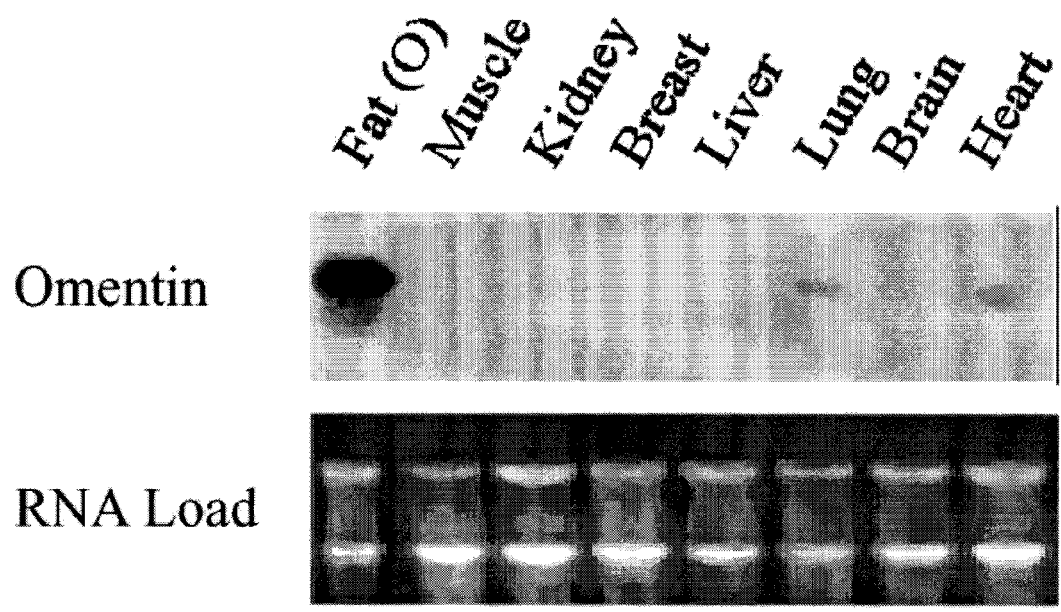
FIGS. 1A and 1B are blots from Northern analyses.
Figure 1B:
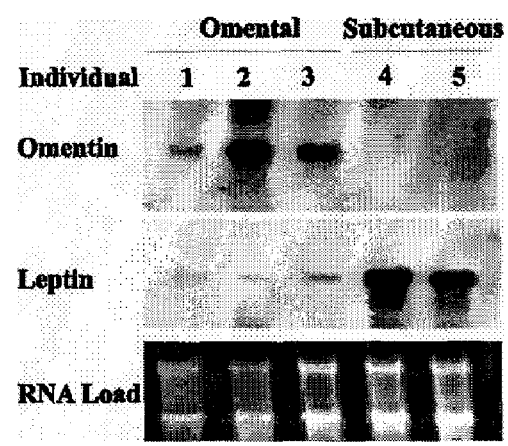

The omentin polypeptide of this invention was isolated and purified from adipose, i.e., fat, tissue. Messenger RNA encoding omentin polypeptide is relatively highly and selectively expressed in omental fat tissue. FIG. 1A shows the results of a multiple tissue Northern analysis blot from a human. As shown in the Northern blot of FIG. 1A, messenger RNA encoding omentin polypeptide is selectively expressed in omental fat tissue, much less in lung and heart, and not at all in muscle, liver, kidney, breast, and brain. FIG. 1B is a Northern blot of adipose tissues from omental and subcutaneous depots of five individual humans. As shown in the Northern blot of FIG. 1B, messenger RNA encoding omentin polypeptide is relatively highly expressed in omental fat, but not in subcutaneous fat. In the Northern analysis represented in FIG. 1B, the blot was reprobed with leptin, showing that leptin is preferentially expressed in subcutaneous fat, and generally not in omental fat, as is generally known in the art. For the Northern analyses resulting in FIGS. 1A and 1B, adipose RNA was prepared with TRIZOL, available from Invitrogen, Carlsbad, Calif., from human tissue. The other RNA samples were obtained from Clontech, Palo Alto, Calif. The Northern analysis was performed by loading 15 μg of total RNA per lane. The human omentin probe, corresponding to bases 263 to 1270 of AY549722 in GenBank, was random-labeled, available from Stratagene, La Jolla, Calif., with $^{32}$P-dCTP. Hybridization was carried out at 65° C. in Rapid-hyb buffer, available from Amersham Biosciences, Piscataway, N.J., and blots were washed twice with 0.5×SSC/1% SDS at 65° C. The RNA loadings were revealed by ethidium bromide staining.

Figures 2A, 2B:
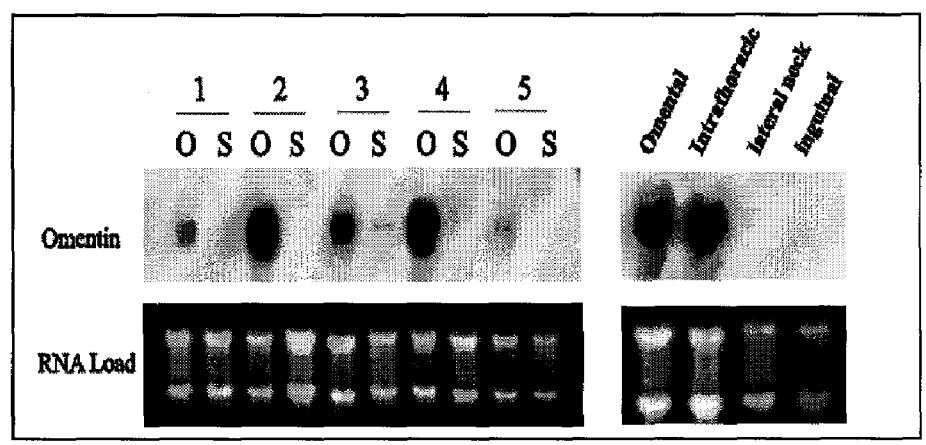
FIGS. 2A and 2B are blots from Northern analyses.

To eliminate the possibility of individual variations in gene expression among different subjects, Northern analysis was also conducted using samples from *Rhesus* monkeys in the manner described above. FIG. 2A is a Northern blot of paired omental (O) adipose tissue and inguinal subcutaneous (S) adipose tissue from five individual *Rhesus* monkeys. As shown in the Northern blot of FIG. 2A, messenger RNA encoding omentin polypeptide was predominantly expressed in omental fat compared to subcutaneous fat from the same animals. FIG. 2B is a Northern blot that shows regional differences in omentin expression in a single *Rhesus* monkey. To help rule out concern of potential contamination from omental structures other than omental fat, adipose tissues from different regions were obtained from a single monkey for Northern analysis. As shown in FIG. 2B, omentin is expressed in intrathoracic as well as in omental fat tissue, but not in the subcutaneous fat tissues from neck and inguina, confirming the visceral pattern of omentin expression.

Figure 3:
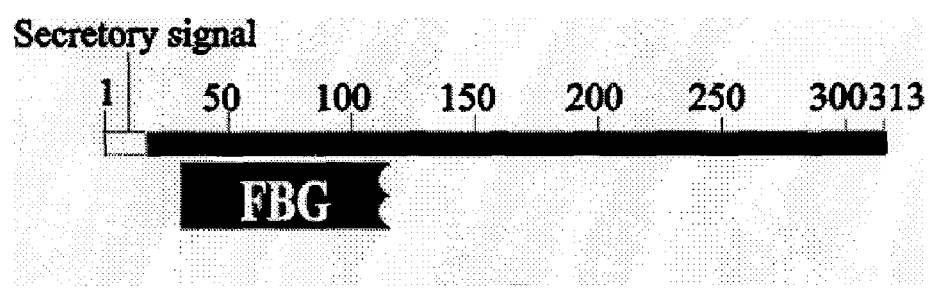
FIG. 3 is a schematic structure of the omentin polypeptide of SEQ ID NO:1.

The omentin polypeptide of SEQ ID NO:1 contains 313 amino acids. The estimated molecular weight is 35 kDa. FIG. 3 is a schematic structure of the omentin polypeptide of SEQ ID NO:1. The N-terminal portion (the end at amino acid 1) of omentin polypeptides contain a hydrophobic region that is typical of a signal sequence for protein secretion, followed by a region homologous to a fibrinogen-related domain (FBG). Such domains are globular structures found in proteins, such as the β and γ chains of fibrinogen, PGAR (PPARγ angiopoietin related), and tenasin. Full-length clones of omentin were obtained from EST sequencing of an omental fat cDNA library, Cat# HL-5028t, available from Clontech. The EST clone was used as a template for PCR amplification of protein-coding regions with appropriate primers. The resultant PCR products were subcloned into proper expression vectors and verified without mutation by sequencing.

Figure 4A:
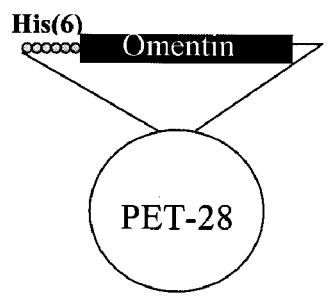
FIG. 4A is a structural representation of a His (6)-tagged omentin polypeptide cDNA in a PET-28 plasmid.
Figure 4B:
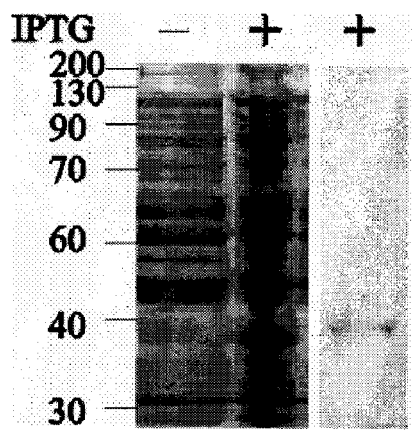
FIG. 4B is a Coomassie Blue stain of bacterial cell lysates expressing recombinant human omentin polypeptide.

In one embodiment of this invention, omentin polypeptide is expressed using a His (6)-tagged omentin cDNA in a bacteria host cell as shown in FIG. 4A. Omentin polypeptide without the signal peptide was cloned into a PET28 vector, available from Novagen, San Diego, Calif., under the control of the T7 promoter. The target gene was introduced into Tuner (DE3) pLacI cells, expressed by IPTG induction, and purified with a nickel column. The omentin-containing bacteria were grown with (+) or without (−) IPTG induction. Cell lysates, shown in the first two lanes of FIG. 4B, and purified protein, shown in lane 3 of FIG. 4C, were analyzed on 4-20% SDS-PAGE and stained with Coomassie Blue.

In one embodiment of this invention, antibodies are formed from the omentin polypeptide. As will be appreciated by one skilled in the art following the teachings herein provided, various methods are available in the art for forming antibodies. For antibody production, cDNA encoding amino acids 73-313 of SEQ ID NO:1 was amplified with primer 1120 and 1121 using high-fidelity PCR system, available from Boehringer Mannheim, Mannheim, Germany, and subcloned into a PET28 vector, available from Novagen, to create the plasmid G6329, which was verified by sequencing and transformed into *Escherichia coli*, available from Novagen. The His(6)-tagged protein was overexpressed by IPTG induction Yang R. Z., Blaileanu G., Hansen B. C., Shuldiner A. R., and Gong D. W., *cDNA cloning, genomic structure, chromosomal mapping, and functional expression of a novel human alanine aminotransferase*, Genomics, 2002 March;79(3):445-50, herein incorporated by reference in its entirety, and purified with Ni2+− NTA resin, available from QIAGEN Inc., Valencia, Calif., under denaturing condition using 8M urea for polyclonal antibody production in rabbits and monoclonal antibody production by AnaSpec, San Jose, Calif.

Figure 4C:
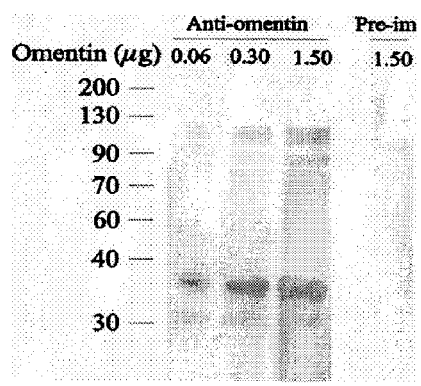
FIG. 4C is a Western blot of recombinant human omentin polypeptide.

A representative immunoblot utilizing antibodies obtained in this manner is shown in FIG. 4C. The indicated amount of recombinant omentin polypeptide was blotted to a nitrocellulose membrane and probed with omentin antiserum or pre-immune serum, followed by a second antibody, such as alkaline phosphatase-labeled goat against rabbit IgG, stained with BCIP/NBT. A clear induction of a recombinant protein was observed at the expected size (about 35 kd) and purified to homogeneity. As shown in FIG. 4C, at about a 1 to 5,000 dilution factor, the antiserum reacts with recombinant omentin polypeptide in a dose-dependent manner, whereas the pre-immune serum shows no staining.

Figure 5:
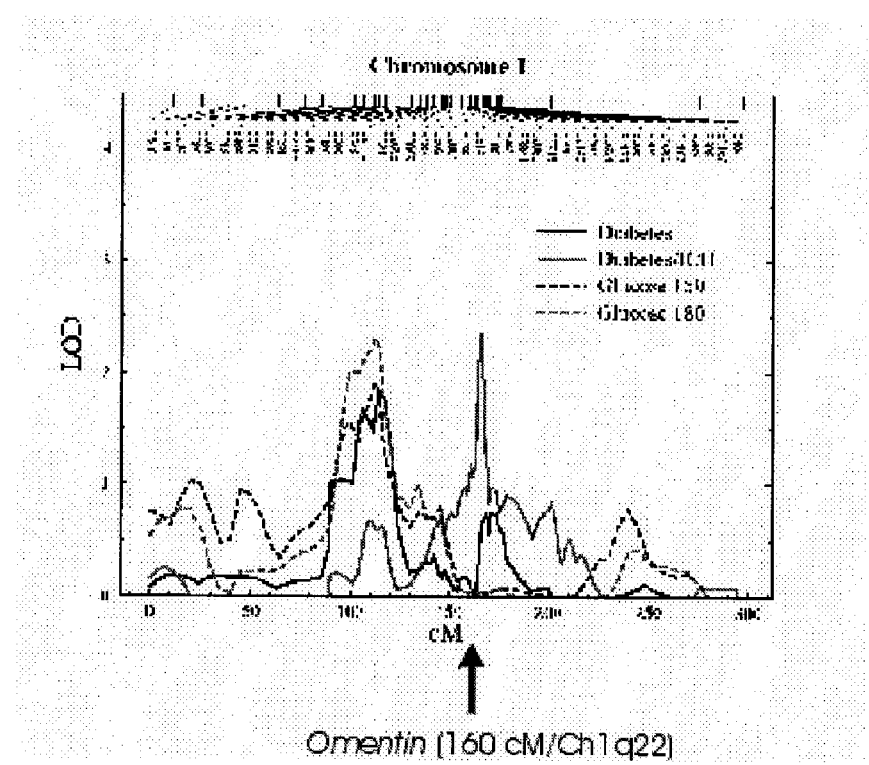
FIG. 5 is a chromosome map showing the location of the omentin gene by its peak linkage to diabetes phenotypes in chromosome 1q21-q23.

The gene encoding omentin polypeptides is localized on a region of human chromosomes generally known to be linked to type 2 diabetes. The omentin gene consists of eight exons and localizes to chromosome 1q22 at 160.1 cM, close to STS marker SHGC-31641. This region of human chromosomes has been linked with type 2 diabetes. FIG. 5 shows, by the arrow, the location of the omentin gene relative to the peak linkage signal at 1q21-q23, known to be linked to diabetes in the Old Order Amish population. As will appreciated by one skilled in the art reviewing FIG. 5, evidence for linkage in this region is stronger for the combined trait of diabetes and impaired glucose homeostasis (lod=2.4) than for diabetes alone (lod=0.92). This region on chromosome 1 is known to represent the most strongly replicated linkage peak for type 2 diabetes. Lod scores reported from other studies corresponding to this region range from 4.3 in Utah Mormons, to 3.0 in collection of French families, to 2.5 in Pima Indians.

Figure 6:
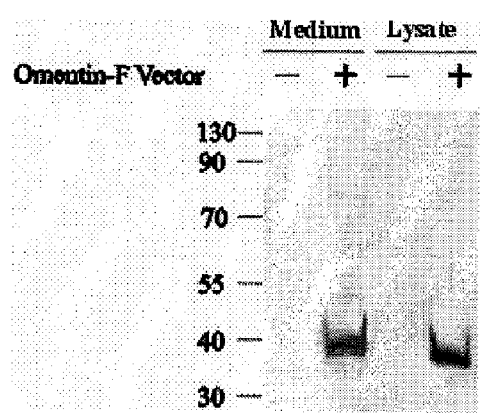
FIG. 6 is an immunoblot of proteins from conditioned medium and cell lysate of example HEK-293 cells stably transfected with an omentin-F vector (+).

As discussed above, omentin polypeptide is a secretory protein. Bacteria-expressed omentin polypeptide is generally insoluble and renaturing efforts generally failed to recover the protein in a soluble fraction. In one embodiment of the invention, to obtain the soluble protein, a flag peptide sequence is tagged to the coding region of omentin polypeptide at the carboxy terminus by polymerase chain reaction (PCR). The PCR product is subcloned into a mammalian expression vector, such as, for example, pcDNA3, available from Invitrogene Corporation, Carlsbad, Calif., driven by a CMV promoter. The resultant plasmid, referred to as omentin-F, is confirmed by sequencing and used to transiently transfect HEK-293T cells using Transfectamine Plus, available from Invitrogene Corporation. The cells are grown in DMEM with 10% FBS. The culture medium was collected and cells are lysed 48 hours after transfection for immunoprecipitation. The fractions are immunoprecipitated with anti-flag M2 affinity beads, available from Sigma-Aldrich, St. Louis, Mo., and blotted with omentin antibody. As a result, omentin-F is detected in both culture media and cell lystate from the cells transfected with omentin-F plasmid, but not from empty vector-transfected control cell. FIG. 6 is an immunoblot of proteins from conditioned medium and cell lysate of example HEK-293 stable transfected with an omentin-F vector (+) according to the above described method, or an empty vector (−). Culture medium, in the amount of about 5 milliliters, and one third of the cell lysates from a 10 centimeter dish were immunoprecipitated with M2-Flag antibody beads. The precipitates were separated on 10% SDS-polyacrylamide gel electrophoresis, immunoblotted with omentin antibodies, and detected with ECL, available from Amersham Biosciences.

Figure 7:
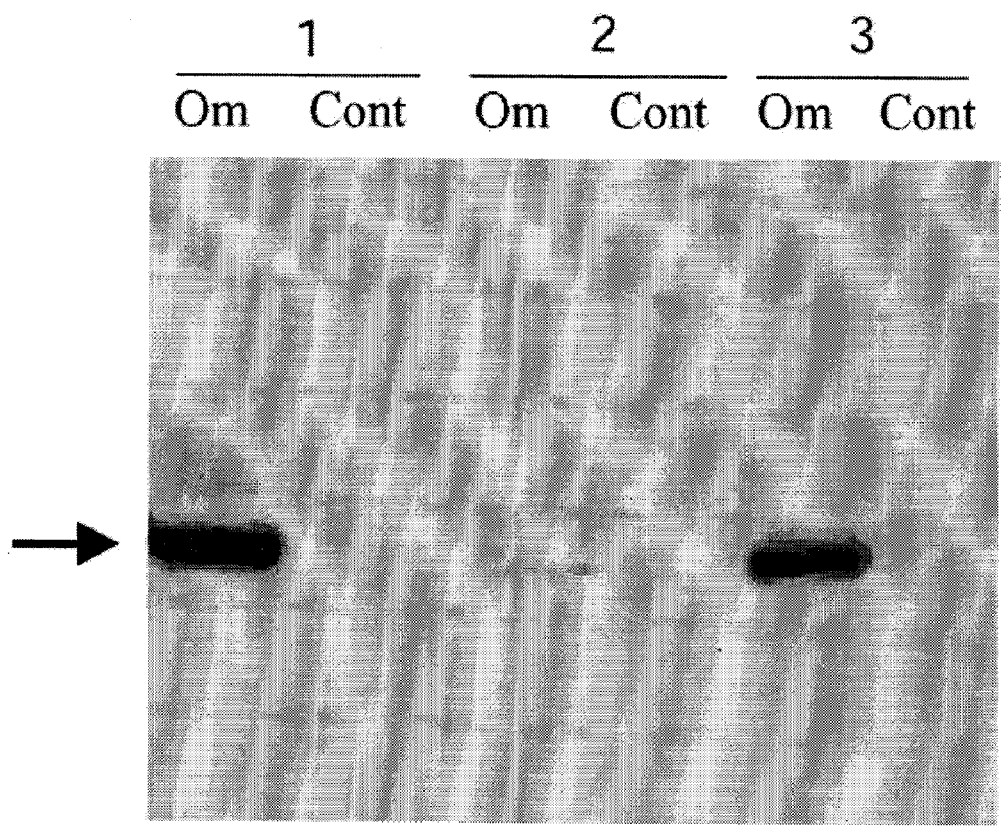
FIG. 7 is a Western blot of three plasma samples immunoprecipitated with omentin antibodies ("Om") and pre-immune antibodies ("Cont").
Figure 8A:
FIGS. 8A-D are photographs of immunofluorescent stained fat tissue.
Figure 8B:
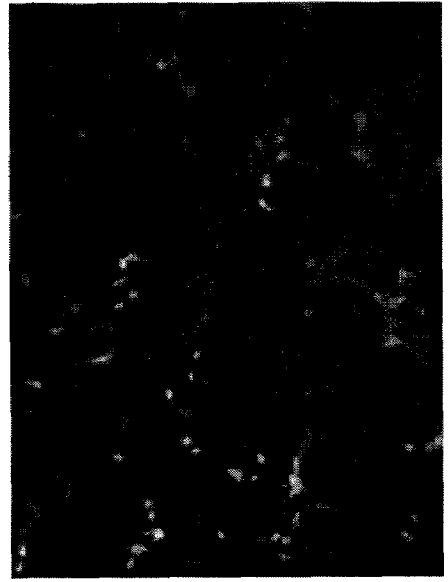
Figure 8C:
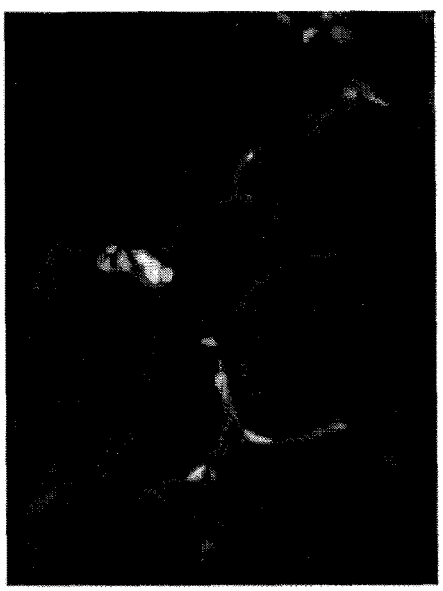
Figure 8D:

Omentin polypeptide was detected in human plasma by immunoprecipitating 3 milliliters of each of three individual plasmas. The three plasma samples were immunoprecipitated with omentin antibodies ("Om") or pre-immune antibodies ("Cont"). The precipitates were analyzed by Western blotting using omentin antiserum or pre-immune serum. FIG. 7 is a Western blot showing the results of the analysis. The arrow indicates the specific band at the expected size (about 38 Kd) of omentin. Cell lysates or immunoprecipitates were separated by SDS-PAGE using 4-20% polyacrylamide gels, available from Gradipore Inc., Hawthorne, N.Y. Following electrophoresis, proteins were transferred onto PVDF membranes and bound proteins were detected by blotting with primary antibody. Immunodetection was achieved by chemiluminescence using ECL, available from Pierce Biotechnology, Rockford, Ill. For human fat explant testing, human biopsy adipose tissues were minced and cultured in 199M medium for 4 hours. The cultured media were concentrated 30 times before being subjected for Western blot analysis with monoclonal anti-omentin 3GXX. For detection of circulating omentin in humans, human plasmas (3 ml, from the Blood Bank of the University of Maryland) were incubated with 20 µl of omentin antiserum or pre-immune (control) and protein A Sepharose beads at 4° C. for 4 hours. The beads were precipitated, washed and subjected to immunoblotting with anti-omentin polyclonal antibody.

Immunofluorescent staining, as shown in FIGS. 8A-D, demonstrates that omentin polypeptide is actually expressed in vivo, and defines the cellular localization. Human adipose tissues was cryosectioned (tissue samples were about 20 µm thick), fixed with 3% paraformaldehyde and permeabilized with 0.5% cold Triton X-100. The tissue slides were then incubated with polyclonal anti-omentin or pre-immune IgG (2.5 mg/ml in PBS) at 1:1000 dilution, washed and re-incubated with a second antibody, goat anti-rabbit IgG-Alexa 568, available from Molecular Probes, Eugene, Oreg. The slides were counterstained with nuclei (DAPI). FIGS. 8A-D show the immunofluorescent staining of the samples. As shown in FIGS. 8A-D, the omentin staining illustrates the unique structure of the adipocyte, with a large central triglyceride storage droplet (round empty circle) and a thin rim of cytoplasm and cell membrane. The fluorescence (lighter portions) is clearly visible in the omentin antibody-stained tissue and much less evident in tissue stained with the pre-immune antibodies. In addition, smaller cells appear to be more intensively stained than the large adipocytes. It is believed that these smaller cells represent stromal vascular cells. FIGS. 8A-D also illustrate that omental, but not subcutaneous, adipose tissue contains immunoreactive omentin polypeptides by immunofluorescence staining. Again it is shown that omentin polypeptides are selectively expressed in the omental adipose tissue.

The selective expression of omentin polypeptide in omental fat tissue and the metabolic effect of omentin polypeptide allow for the use of omentin polypeptides in diagnosing and treating injuries or diseases of or related to adipose tissue. In one embodiment of this invention, a method of modifying at least one of insulin action and glucose metabolism in an animal includes determining an amount of omentin polypeptide in the animal. The amount of omentin polypeptide in the animal can be modified as needed to obtain a desired result. The methods of this invention can include one or more of any of the omentin polypeptides disclosed herein, including the polypeptides having an amino acid sequence of one of SEQ ID NO:1 and SEQ ID NO:3, and homologous variants thereof.

In one embodiment of the invention, modifying the amount of the omentin polypeptide in the animal includes increasing the amount of omentin polypeptide in the animal. The amount of omentin polypeptide can be increased by administering omentin polypeptide to the animal. In another embodiment of the invention, the amount of omentin polypeptide in the animal can be modified by decreasing or interfering with the omentin polypeptide in the animal. The metabolic function of at least a portion of the omentin polypeptide in the animal can be interfered with by introducing an amount of a molecule that regulates signaling or functioning of the omentin polypeptide. As will be appreciated by one skilled in the art following the teachings herein provided, in one embodiment of this invention, the molecule is any molecule that interferes with receptor binding of the omentin polypeptide. Examples of such molecules, include, for example, antibodies or other proteins or polypeptides. By increasing or decreasing the effective amount of omentin, the method of this invention can be used to therapeutically treat an undesirable condition of tissue or a disease, such as obesity and type 2 diabetes, such as by modifying or manipulating glucose metabolism.

In another embodiment of this invention, the omentin polypeptide is used in a method of inducing glucose uptake by at least one of animal cells, tissues, and organs, such as, for example adipose tissue, adipocytes, the liver and cells and tissues thereof, the brain and cells and tissues thereof, muscles and cells and tissues thereof, the kidney and cells and tissues thereof. The method includes administering an omentin polypeptide to either the animal in vivo, or adipocytes in vitro. The omentin polypeptide can include one or more of any of the variants of omentin polypeptide described above. In one embodiment of the invention, the administered omentin polypeptide enhances insulin-mediated glucose transport in the adipocytes, thereby inducing glucose uptake by animal adipocytes. In another embodiment the administered omentin polypeptide activates, either directly or indirectly, the polypeptide kinase Akt/PKB, thereby inducing glucose uptake by animal adipocytes.

In one embodiment of this invention, omentin polypeptide can be used to increase insulin-stimulated 2-deoxyglucose transport. To demonstrate omentin polypeptide effect on insulin-stimulated 2-deoxyglucose transport, a cassette of pIRES2-hrGFP, available from Stratagene, was subcloned in pcDNA3 backbone via appropriate shuttle vectors, thereby creating the plasmid G6422. The plasmid was transfected into mammalian HEK-293T cells and the top 10% of cells with highest fluorescence, sorted by fluorescence-activated cell sorting (FACS), were collected and cultured. The cells were grown in 10% FBS DMEM medium, available from Invitrogen, Carlsbad, Calif., to 80% confluency and then in serum-free DMEM for 5 days. The conditioned medium was subjected to SuperQ anion ion exchange chromatography, available from Tosoh Biosciences, Montgomeryville, Pa., and the omentin-containing fractions were pooled for galactose-affinity chromatography, available from Pierce Biotechnology, Inc. The protein was eluted with a buffer containing 10 mM Tris-1 mM EDTA (at about pH 8) and used for analysis and the elution buffer was used as control. Typically, 3 liters of cell culture media yield about 100 μg omentin-F. The secretion of omentin into the medium was verified by Western blotting with omentin antibody. Cells with the highest omentin expression were selected and then cultured first in growth medium (DMEM/10% FBS) and then replaced with serum-free medium (DMEM only) for 48 hours.

Figure 9:
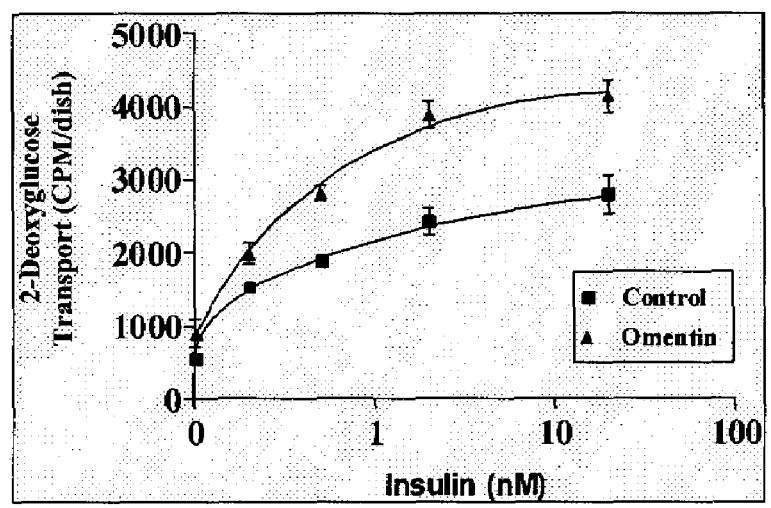
FIG. 9 is a graphical representation of the results of a glucose transport assay.

The conditioned media were collected and concentrated 100 times with CENTRICON-80 filters (Millipore, 10 kDa filter) for a glucose transport assay using differentiated 3T3-L1 adipocytes. The glucose transport assay was conducted according to Kashiwagi A., Verso M. A., Andrews J., Vasquez B., Reaven G., Foley J. E., *In vitro insulin resistance of human adipocytes isolated from subjects with noninsulin-dependent diabetes mellitus*, J Clin Invest. 1983 October; 72(4):1246-54, herein incorporated by reference in its entirety. Briefly stated, human adipocytes were isolated by collegenase digestion and centrifugation. The cells were incubated with omentin (500 ng/ml) for 30 minutes and stimulated by insulin (60 nM) for 5 min. The glucose transport was determined by measuring the uptake of a trace concentration of glucose. The results of the glucose transport assay are represented in FIG. 9. As shown in FIG. 9, omentin polypeptide stimulates the glucose uptake at all insulin concentrations tested. The omentin polypeptide exhibited its largest effect (1.5 to 2-fold increase) on insulin-stimulation between 2 and 20 nM.

Figure 10:
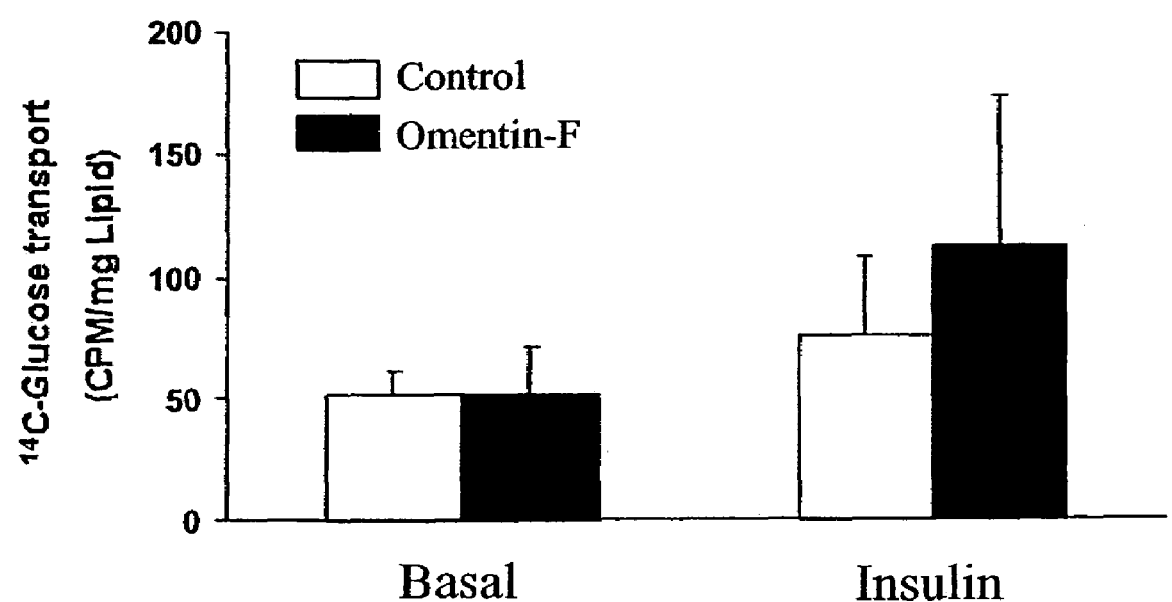
FIG. 10 is a graphical representation of the results of a glucose to transport assay.

To further demonstrate the affect of omentin polypeptide on insulin-signaling, adipocytes from human fat tissue were isolated and exposed to insulin with or without pretreatment of omentin polypeptide. FIG. 10 is a graphical representation of the results of the analysis. As shown in FIG. 10, insulin stimulated the uptake of [14C]2-deoxyglucose about 50%. An additional 20-30% more glucose uptake was observed with the pretreatment of omentin (30 minutes before insulin).

Figure 11:
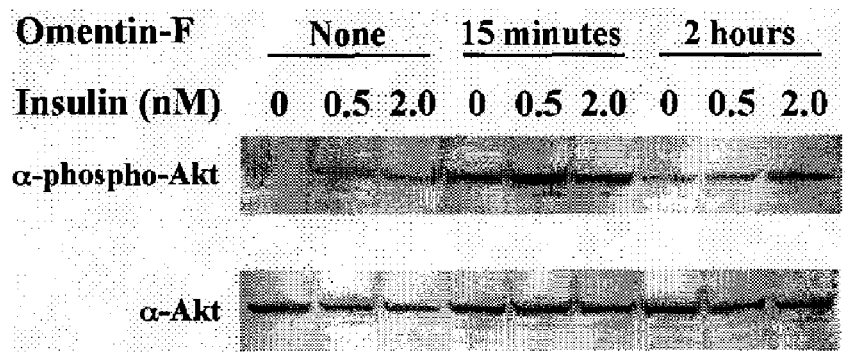
FIG. 11 is a Western blot showing Akt kinase phosporylation by acute and chronic exposure to omentin-F.

Omentin polypeptides stimulate Akt kinase acutely and synergistically with insulin. Akt kinase is activated by insulin and other growth factors, and is a central molecule mediating cell growth, proliferation, and apoptosis. Activation of Akt kinase requires phosphorylation at threonine (T308) and serine (S473) residues. To demonstrate omentin polypeptide affect on Akt phosphorylation, isolated adipocytes were incubated with omentin polypeptide for various times and then treated with or without insulin (60 nM). The reaction was stopped by adding lysis buffer containing 2%SDS, 62.5 mM Tris-HCl, pH 6.8 at 90° C., followed by sonication for 15 seconds. The resultant lysates were subjected to immunoblotting analysis with a mixture of two phosphor-specific antibodies against the phosphorylated Akt or with general Akt antibody for total Akt in the lysates. Omentin polypeptide activated Akt kinase acutely, within about 15 minutes, by a treatment with serum-free conditioned medium (about 200 ng/ml omentin). Additional activation of Akt kinase by omentin polypeptide was observed in the presence of insulin, indicating a synergistic effect between the two factors. FIG. 11 shows Akt kinase phosporylation by acute and chronic exposure to omentin-F. Adipocytes (3T3-L1) were exposed to omentin-F for 15 minutes and 2 hours, followed by stimulation with 0, 0.5, or 2 nM insulin for five minutes. Cell lysates were immunoblotted with Akt antibodies for Western blotting. As shown in the Western blot of FIG. 11, after a two-hour exposure to omentin polypeptide, when maximal effects on glucose transport were observed, activation of Akt kinase was lower but still elevated over the control ("None").

To demonstrate the impact of omentin polypeptide on glucose uptake in adipocytes in vivo, mice were administered intraperitoneally with omentin polypeptide (1 μg/g body weight) or control vehicle (PBS) 30 minutes prior to administering glucose. To obtain large quantity of omentin for animal study, the signal peptide of omentin (16 amino acids at the amino-terminal) was replaced with a His (6) tag and the fusion protein was expressed in bacteria using a similar approach as described in Yang et al., previously incorporated by reference in its entirety. The bacterially-expressed omentin was an inclusion body and insoluble. The inclusion body was purified and was dissolved in CAPS, available from Novagen, according to the manufacture's protocol. The solublized protein was dialyzed and further purified by gel filtration with Hload 16/60 Superdex 200, available from Amersham Biosciences, into homogeneity. C57/BL mice were obtained from Jackson Laboratory, Bar Harbor, Me. The mice were housed on a 12-hour light/dark cycle and allowed free access to standard mouse food and water. The mice were used for testing were at 7-10 weeks of age. For testing, the mice fasted overnight and received an intraperitoneal injection of omentin (1 μg/g body weight) or only vehicle, as a control, 30 min before an intraperitoneal injection of glucose load at 2mg/g body weight. Blood samples were obtained via tail veins at the indicated times before and after the glucose injection. Blood glucose concentrations were measured with an ACCU-CHEK blood glucometer, available from Roche Diagnostics, Indianapolis, Ind.

Figure 12:
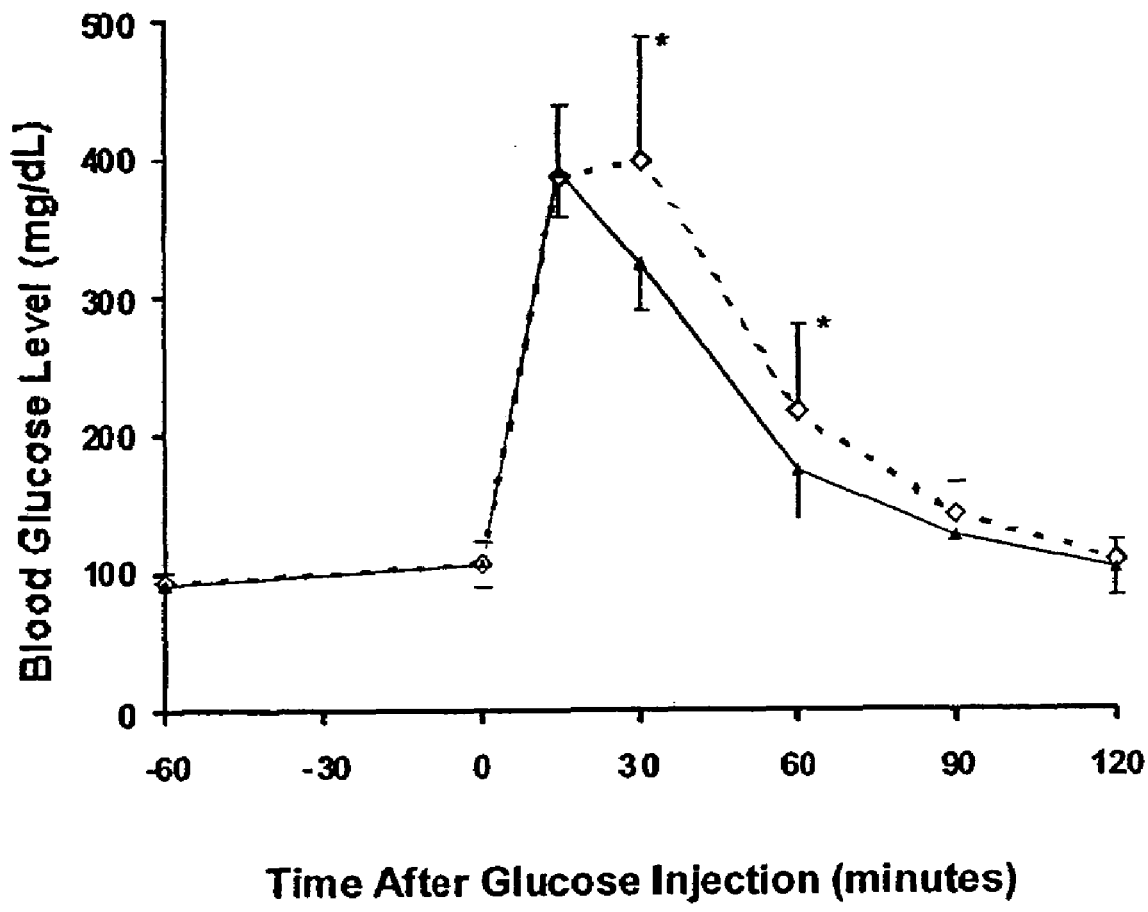
FIG. 12 is a graphical representation of the results of an in vivo glucose transport test.

FIG. 12 is a graphical representation of the results of the analysis. Upon intraperitoneal glucose injection, blood glucose levels in the mice rose rapidly from roughly 100 to 400 mg/dl within 15 minutes in both groups. However, the glucose levels in the control group (dotted line) peaked at about 30 minutes and decreased thereafter. In contrast, the glucose levels in omentin-administered group (solid line) began to drop from 30 minutes, and were lower than the control group over the two hour period. This result demonstrates that omentin polypeptide improves glucose disposal in vivo.

Omentin polypeptide thus enhances insulin action by stimulating insulin-mediated glucose uptake or disposal and improves glucose tolerance.

The invention additionally relates to a method of diagnosing or detecting a disease or condition involving animal tissue that contains, metabolically uses, or expresses omentin polypeptide in an animal suspected of having the disease or condition. In one embodiment of this invention, a first step of the method includes contacting a sample of bodily fluid from the animal with a plurality of antibodies adapted to specifically bind omentin polypeptide. The antibodies bound to omentin polypeptides in the sample can then be detected and measured. As will be appreciated from the discussions above, levels of omentin polypeptide vary within different humans or other animals. By comparing the measured amount to a control, the omentin polypeptide can be used to diagnose or detect a disease or condition, particularly those of or related to particular tissues, such as, for example, liver tissue, brain tissue, muscle tissue, adipose tissue, and kidney tissue. The bodily fluid from the animal used for testing can include, without limitation, blood, serum, lymph, urine, sweat, mucus, sputum, saliva, semen, spinal fluid, interstitial fluid, synovial fluid, cerebrospinal fluid, gingival fluid, vaginal fluid, and pleural fluid.

As omentin polypeptides are secreted and measurable in a human or other animal, another aspect of this invention includes diagnostic tests and kits for detecting and/or measuring the amount or level of omentin polypeptide in a human or other animal. The omentin polypeptide level in a human or other animal can be used for testing for particular diseases, such as, for example, obesity and type 2 diabetes, or a susceptibility to such diseases.

One embodiment of this invention includes a method of detecting omentin polypeptide, or the amount thereof, in bodily fluids of an animal. In one particularly preferred embodiment of this invention, the method includes first contacting a sample of the bodily fluids with at least one antibody that specifically binds to the omentin polypeptide. Then, the antibody bound to the omentin polypeptide in the sample is detected and, optionally, measured, such as by means available and know in the art. The bodily fluid to be tested can be any bodily fluid including blood, serum, lymph, urine, sweat, mucus, sputum, saliva, semen, spinal fluid, interstitial fluid, synovial fluid, cerebrospinal fluid, gingival fluid, vaginal fluid, and pleural fluid. The omentin polypeptide can be any omentin polypeptide disclosed herein, including variants thereof not particularly disclosed.

The invention additionally includes a diagnostic kit for use in diagnosing damage or disease in tissue containing or expressing omentin polypeptide. In one particularly preferred embodiment of this invention, the diagnostic kit includes a measurer of an amount of omentin polypeptide in a sample of bodily fluids. The measurer, for example, can include a biologic assay, an antibody-based assay, an enzyme linked imnmunosorbent assay, a Western blot, a rapid immunoassay, and a radioimmunoassay. The diagnostic kit also includes an indicator, such as, for example, a control or a list of predetermined values for comparison, for determining if a measurement taken by the measurer is in a predetermined range associated with damage or disease in the tissue.

Thus, the invention provides isolated polypeptides that selectively express in fat tissue as well as methods for use of the polypeptide. The polypeptides can be used therapeutically to regulate or modify glucose metabolism, thereby providing a therapeutic agent for diseases, or in a diagnostic test or kit for detecting diseases.

The invention illustratively disclosed herein suitably may be practiced in the absence of any element, part, step, component, or ingredient which is not specifically disclosed herein.

While in the foregoing detailed description this invention has been described in relation to certain preferred embodiments thereof, and many details have been set forth for purposes of illustration, it will be apparent to those skilled in the art that the invention is susceptible to additional embodiments and that certain of the details described herein can be varied considerably without departing from the basic principles of the invention.

What is claimed is:

1. A method of increasing glucose metabolism in an animal comprising administering to the animal a polypeptide comprising an amino acid sequence of one of SEQ ID NO:1 or SEQ ID NO:3, wherein said administration increases glucose metabolism in the animal.

2. The method of claim 1, wherein the polypeptide comprises the amino acid sequence of SEQ ID NO:1.

3. The method of claim 1, wherein the polypeptide comprises the amino acid sequence of SEQ ID NO:3.

4. A method of increasing insulin-mediated glucose uptake in an animal comprising administering to the animal a polypeptide comprising an amino acid sequence of one of SEQ ID NO:1 or SEQ ID NO:3, wherein said administration increases the insulin-mediated glucose uptake in the animal.

5. The method of claim 4, wherein the polypeptide comprises the amino acid sequence of SEQ ID NO:1.

6. The method of claim 4, wherein the polypeptide comprises the amino acid sequence of SEQ ID NO:3.

7. A method of increasing insulin-stimulated glucose transport in an animal, the method comprising administering to the animal a polypeptide comprising an amino acid sequence of one of SEQ ID NO:1 or SEQ ID NO:3, wherein said administration increases the insulin-stimulated glucose transport in the animal.

8. The method of claim 7, wherein the polypeptide comprises the amino acid sequence of SEQ ID NO:1.

9. The method of claim 7, wherein the polypeptide comprises the amino acid sequence of SEQ ID NO:3.

10. The method of claim 7, wherein said administration further comprises activation of Akt kinase.

11. The method of claim 10, wherein the activation of Akt kinase comprising an increase in phosphorylation of said Akt kinase.

12. A method of treating a disease or condition in an animal involving animal tissue that contains, uses, or expresses omentin polypeptide comprising administering to the animal an omentin polypeptide having an amino acid sequence of SEQ ID NO:1, wherein said administration increases the amount of omentin polypeptide in the animal tissue of the animal, and wherein said disease or condition is central obesity, type 2 diabetes or hyperinsulinemia.

13. The method of claim 12, wherein the animal tissue comprises stromal vascular cells, pancreas, muscle, liver or adipose tissue.

14. The method of claim 12, wherein the animal tissue is adipose tissue.

15. The method of claim 14, wherein the adipose tissue is omental adipose tissue.

16. A method of treating a disease or condition in an animal involving animal tissue that contains, uses, or expresses omentin polypeptide comprising administering to the animal an omentin polypeptide having an amino acid sequence of SEQ ID NO:3, wherein said administration increases the amount of omentin polypeptide in the animal tissue of the animal, and wherein said disease or condition is central obesity, type 2 diabetes, cardiovascular disease, dyslipidemia, hypertension or hyperinsulinemia.

17. The method of claim 16, wherein the animal tissue comprises stromal vascular cells, pancreas, muscle, liver or adipose tissue.

18. The method of claim 16, wherein the animal tissue is adipose tissue.

19. The method of claim 18, wherein the adipose tissue is omental adipose tissue.

\* \* \* \* \*

UNITED STATES PATENT AND TRADEMARK OFFICE
CERTIFICATE OF CORRECTION

| | |
|---|---|
| PATENT NO. | : 7,312,197 B2 |
| APPLICATION NO. | : 10/785720 |
| DATED | : December 25, 2007 |
| INVENTOR(S) | : Da-Wei Gong et al. |

Page 1 of 1

It is certified that error appears in the above-identified patent and that said Letters Patent is hereby corrected as shown below:

Delete Column 1, lines 16-19 and replace with --This invention was made with government support under NIH Grant Number DK57835, awarded by the National Institutes of Health. The U.S. Government has certain rights in the invention.--

Signed and Sealed this

Sixth Day of May, 2008

JON W. DUDAS
*Director of the United States Patent and Trademark Office*

SEQUENCE LISTING

<160> NUMBER OF SEQ ID NOS: 4

<210> SEQ ID NO 1
<211> LENGTH: 313
<212> TYPE: PRT
<213> ORGANISM: Homo sapiens

<400> SEQUENCE: 1

```
Met Asn Gln Leu Ser Phe Leu Leu Phe Leu Ile Ala Thr Thr Arg Gly
1               5                   10                  15

Trp Ser Thr Asp Glu Ala Asn Thr Tyr Phe Lys Glu Trp Thr Cys Ser
            20                  25                  30

Ser Ser Pro Ser Leu Pro Arg Ser Cys Lys Glu Ile Lys Asp Glu Cys
        35                  40                  45

Pro Ser Ala Phe Asp Gly Leu Tyr Phe Leu Arg Thr Glu Asn Gly Val
    50                  55                  60

Ile Tyr Gln Thr Phe Cys Asp Met Thr Ser Gly Gly Gly Gly Trp Thr
65                  70                  75                  80

Leu Val Ala Ser Val His Glu Asn Asp Met Arg Gly Lys Cys Thr Val
                85                  90                  95

Gly Asp Arg Trp Ser Ser Gln Gln Gly Ser Lys Ala Val Tyr Pro Glu
            100                 105                 110

Gly Asp Gly Asn Trp Ala Asn Tyr Asn Thr Phe Gly Ser Ala Glu Ala
```

```
                 115                 120                 125
Ala Thr Ser Asp Asp Tyr Lys Asn Pro Gly Tyr Tyr Asp Ile Gln Ala
    130                 135                 140

Lys Asp Leu Gly Ile Trp His Val Pro Asn Lys Ser Pro Met Gln His
145                 150                 155                 160

Trp Arg Asn Ser Ser Leu Leu Arg Tyr Arg Thr Asp Thr Gly Phe Leu
                165                 170                 175

Gln Thr Leu Gly His Asn Leu Phe Gly Ile Tyr Gln Lys Tyr Pro Val
            180                 185                 190

Lys Tyr Gly Glu Gly Lys Cys Trp Thr Asp Asn Gly Pro Val Ile Pro
        195                 200                 205

Val Val Tyr Asp Phe Gly Asp Ala Gln Lys Thr Ala Ser Tyr Tyr Ser
    210                 215                 220

Pro Tyr Gly Gln Arg Glu Phe Thr Ala Gly Phe Val Gln Phe Arg Val
225                 230                 235                 240

Phe Asn Asn Glu Arg Ala Ala Asn Ala Leu Cys Ala Gly Met Arg Val
                245                 250                 255

Thr Gly Cys Asn Thr Glu His His Cys Ile Gly Gly Gly Tyr Phe
            260                 265                 270

Pro Glu Ala Ser Pro Gln Gln Cys Gly Asp Phe Ser Gly Phe Asp Trp
        275                 280                 285

Ser Gly Tyr Gly Thr His Val Gly Tyr Ser Ser Arg Glu Ile Thr
    290                 295                 300

Glu Ala Ala Val Leu Leu Phe Tyr Arg
305                 310

<210> SEQ ID NO 2
<211> LENGTH: 1284
<212> TYPE: DNA
<213> ORGANISM: Homo sapiens

<400> SEQUENCE: 2
ggcattgtgc cagggagggg tgaggctgga aaccttggtt ggccccactg ggcttcctcc        60
ataaagcttt ctgcacctca ttccacatca ggagcgtttt tggagaaagc tgcactctgt      120
tgagctccag ggcgcagtgg agggagggag tgaaggagct ctctgtaccc aaggaaagtg      180
cagctgagac tcagacaaga ttacaatgaa ccaactcagc ttcctgctgt ttctcatagc      240
gaccaccaga ggatggagta cagatgaggc taatacttac ttcaaggaat ggacctgttc      300
ttcgtctcca tctctgccca gaagctgcaa ggaaatcaaa gacgaatgtc ctagtgcatt      360
tgatggcctg tattttctcc gcactgagaa tggtgttatc taccagacct tctgtgacat      420
gacctctggg ggtggcggct ggaccctggt ggccagcgtg catgagaatg acatgcgtgg      480
gaagtgcacg gtgggcgatc gctggtccag tcagcagggc agcaaagcag actacccaga      540
gggggacggc aactgggcca actacaacac ctttggatct gcagaggcgg ccacgagcga      600
tgactacaag aaccctggct actacgacat ccaggccaag gacctgggca tctggcacgt      660
gcccaataag tccccatgc agcactggag aaacagctcc ctgctgaggt accgcacgga      720
cactggcttc ctccagacac tgggacataa tctgtttggc atctaccaga aatatccagt      780
gaaatatgga gaaggaaagt gttggactga caacggcccg gtgatcctg tggtctatga      840 ttttggcgac gcccagaaaa cagcatctta ttactcaccc tatggccagc gggaattcac      900
tgcgggattt gttcagttca gggtatttaa taacgagaga gcagccaacg ccttgtgtgc      960
tggaatgagg gtcaccggat gtaacactga gcaccactgc attggtggag gaggatactt     1020
```

```
tccagaggcc agtccccagc agtgtggaga ttttttctggt tttgattgga gtggatatgg   1080
aactcatgtt ggttacagca gcagccgtga gataactgag gcagctgtgc ttctattcta   1140
tcgttgagag ttttgtggga gggaacccag acctctcctc ccaaccatga gatcccaagg   1200
atggagaaca acttacccag tagctagaat gttaatggca gaagagaaaa caataaatca   1260
tattgactca aaaaaaaaaa aaaa                                           1284
```

<210> SEQ ID NO 3
<211> LENGTH: 325
<212> TYPE: PRT
<213> ORGANISM: Homo sapiens

<400> SEQUENCE: 3

```
Met Leu Ser Met Leu Arg Thr Met Thr Arg Leu Cys Phe Leu Leu Phe
  1               5                  10                  15

Phe Ser Val Ala Thr Ser Gly Cys Ser Ala Ala Ala Ser Ser Leu
             20                  25                  30

Glu Met Leu Ser Arg Glu Phe Glu Thr Cys Ala Phe Ser Phe Ser Ser
         35                  40                  45

Leu Pro Arg Ser Cys Lys Glu Ile Lys Glu Arg Cys His Ser Ala Gly
 50                  55                  60

Asp Gly Leu Tyr Phe Leu Arg Thr Lys Asn Gly Val Val Tyr Gln Thr
 65                  70                  75                  80

Phe Cys Asp Met Thr Ser Gly Gly Gly Gly Trp Thr Leu Val Ala Ser
                 85                  90                  95

Val His Glu Asn Asp Met Arg Gly Lys Cys Thr Val Gly Asp Arg Trp
            100                 105                 110

Ser Ser Gln Gln Gly Asn Lys Ala Asp Tyr Pro Glu Gly Asp Gly Asn
        115                 120                 125

Trp Ala Asn Tyr Asn Thr Phe Gly Ser Ala Glu Ala Ala Thr Ser Asp
130                 135                 140

Asp Tyr Lys Asn Pro Gly Tyr Tyr Asp Ile Gln Ala Lys Asp Leu Gly
145                 150                 155                 160

Ile Trp His Val Pro Asn Lys Ser Pro Met Gln His Trp Arg Asn Ser
                165                 170                 175

Ala Leu Leu Arg Tyr Arg Thr Asn Thr Gly Phe Leu Gln Arg Leu Gly
            180                 185                 190

His Asn Leu Phe Gly Ile Tyr Gln Lys Tyr Pro Val Lys Tyr Arg Ser
        195                 200                 205

Gly Lys Cys Trp Asn Asp Asn Gly Pro Ala Ile Pro Val Val Tyr Asp
    210                 215                 220

Phe Gly Asp Ala Lys Lys Thr Ala Ser Tyr Tyr Ser Pro Tyr Gly Gln
225                 230                 235                 240

Arg Glu Phe Val Ala Gly Phe Val Gln Phe Arg Val Phe Asn Asn Glu
                245                 250                 255

Arg Ala Ala Asn Ala Leu Cys Ala Gly Ile Lys Val Thr Gly Cys Asn
            260                 265                 270

Thr Glu His His Cys Ile Gly Gly Gly Gly Phe Phe Pro Gln Gly Lys
        275                 280                 285

Pro Arg Gln Cys Gly Asp Phe Ser Ala Phe Asp Trp Asp Gly Tyr Gly
    290                 295                 300

Thr His Val Lys Ser Ser Cys Ser Arg Glu Ile Thr Glu Ala Ala Val
305                 310                 315                 320
```

```
Leu Leu Phe Tyr Arg
            325

<210> SEQ ID NO 4
<211> LENGTH: 1150
<212> TYPE: DNA
<213> ORGANISM: Homo sapiens

<400> SEQUENCE: 4 gcagggagc  tccgagtgtc  cacaggaagg  gaactatcag  ctcctggcat  ctgtaaggat    60
gctgtccatg  ctgaggacaa  tgaccagact  ctgcttcctg  ttattcttct  ctgtggccac   120
cagtgggtgc  agtgcagcag  cagcctcttc  tcttgagatg  ctctcgaggg  aattcgaaac   180
ctgtgccttc  tccttttctt  ccctgcctag  aagctgcaaa  gaaatcaagg  aacgctgcca   240
tagtgcaggt  gatggcctgt  attttctccg  caccaagaat  ggtgttgtct  accagacctt   300
ctgtgacatg  acttctgggg  gtggcggctg  gaccctggtg  gccagcgtgc  acgagaatga   360
catgcgtggg  aagtgcacgg  tgggtgatcg  ctggtccagt  cagcagggca  acaaagcaga   420
ctacccagag  ggggatggca  actgggccaa  ctacaacacc  tttggatctg  cagaggcggc   480
cacgagcgat  gactacaaga  accctggcta  ctacgacatc  caggccaagg  acctgggcat   540
ctggcatgtg  cccaacaagt  cccccatgca  gcattggaga  aacagcgccc  tgctgaggta   600
ccgcaccaac  actggcttcc  tccagagact  gggacataat  ctgtttggca  tctaccagaa   660
atacccagtg  aaatacagat  cagggaaatg  ttggaatgac  aatggcccag  ccatacctgt   720
ggtctatgac  tttggtgatg  ctaagaagac  tgcatcttat  tactccaccgt  atggtcaacg   780 ggaatttgtt  gcaggattcg  ttcagttccg  ggtgtttaat  aacgagagag  cagccaacgc   840
cctttgtgct  gggataaaag  ttactggctg  taacactgag  catcactgca  tcggtggagg   900
agggttcttc  ccacagggca  aaccccgtca  gtgtggggac  ttctccgcct  ttgactggga   960
tggatatgga  actcacgtta  agagcagctg  cagtcgggga  ataacggagg  cggctgtact  1020
cttgttctat  agatgagaca  gagctctgcg  gtgtcagggc  gagaacccat  cttccaaccc  1080
cggctatttg  gagacggaaa  aactggaatt  ctaacaagga  ggagaggaga  ctaaatcaca  1140
tcaatttgca                                                             1150
```